United States Patent
Rodger et al.

(10) Patent No.: US 7,326,649 B2
(45) Date of Patent: Feb. 5, 2008

(54) PARYLENE-BASED FLEXIBLE MULTI-ELECTRODE ARRAYS FOR NEURONAL STIMULATION AND RECORDING AND METHODS FOR MANUFACTURING THE SAME

(75) Inventors: Damien C. Rodger, Los Angeles, CA (US); Mark Humayun, Glendale, CA (US); Yu-Chong Tai, Pasadena, CA (US); James D. Weiland, Valencia, CA (US)

(73) Assignees: University of Southern California, Los Angeles, CA (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 11/130,814

(22) Filed: May 16, 2005

(65) Prior Publication Data
US 2006/0003090 A1    Jan. 5, 2006

Related U.S. Application Data

(60) Provisional application No. 60/571,031, filed on May 14, 2004.

(51) Int. Cl.
 *H01L 21/44* (2006.01)
(52) U.S. Cl. .............. 438/669; 438/458; 438/660; 438/674; 257/737; 257/E21.001
(58) Field of Classification Search ............... 438/119, 438/458, 660, 669, 674; 257/737, 774, E21.007
See application file for complete search history.

(56) References Cited

U.S. PATENT DOCUMENTS

| | | | |
|---|---|---|---|
| 6,168,948 B1 * | 1/2001 | Anderson et al. | 435/287.2 |
| 6,280,640 B1 * | 8/2001 | Hurwitz et al. | 216/15 |
| 2002/0050456 A1 * | 5/2002 | Sheppard et al. | 204/451 |
| 2002/0187260 A1 * | 12/2002 | Sheppard et al. | 427/248.1 |
| 2003/0199116 A1 * | 10/2003 | Tai et al. | 438/53 |
| 2005/0205961 A1 * | 9/2005 | Doong | 257/499 |
| 2005/0253273 A1 * | 11/2005 | Tai et al. | 257/774 |
| 2006/0007983 A1 * | 1/2006 | Tai et al. | 374/121 |
| 2006/0018360 A1 * | 1/2006 | Tai et al. | 374/121 |

OTHER PUBLICATIONS

Suzuki T, Mabuchi K and Takeuchi S 2003 A 3D flexible parylene probe array for multichannel neural recording IEEE Neural Eng. 154-6.*
Takeuchi S et al 2004 3D flexible multichannel neural probe array J. Micromech. Microeng. 14 104-7.*
G. H. Feng and E. S. Kim, "Universal concept for fabricating micron to millimeter sized 3-D parylene structures on rigid and flexible substrates," in Proc. IEEE 15th Internal Conference on Micro Electro Mechanical System, Kyoto, Japan, 2003, pp. 594-597.*

* cited by examiner

*Primary Examiner*—Fernando L. Toledo
*Assistant Examiner*—Jarrett J Stark
(74) *Attorney, Agent, or Firm*—Townsend and Townsend and Crew LLP; Gerald T. Gray

(57) ABSTRACT

Method for manufacturing a parylene-based electrode array that includes an underlying parylene layer, one or more patterned electrode layers comprising a conductive material such as a metal, and one or more overlying parylene layers. The overlying parylene is etched away or otherwise processed to expose the electrodes where stimulation or recording is to occur. All other conductive material in the device is occluded from the environment by the two layers of parylene surrounding it.

16 Claims, 8 Drawing Sheets

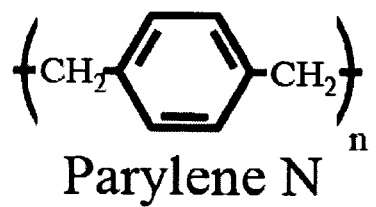
Parylene N
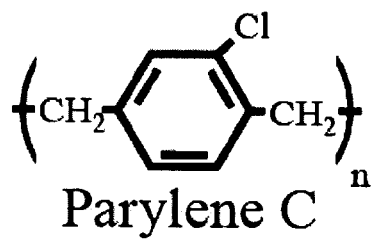
Parylene C
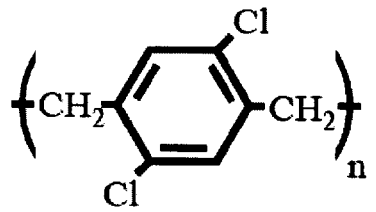
Parylene D
FIG. 1: Chemical structures of the three most commonly employed parylenes. Parylene C is preferred because of its mechanical strength, biocompatibility, and low moisture permeability.

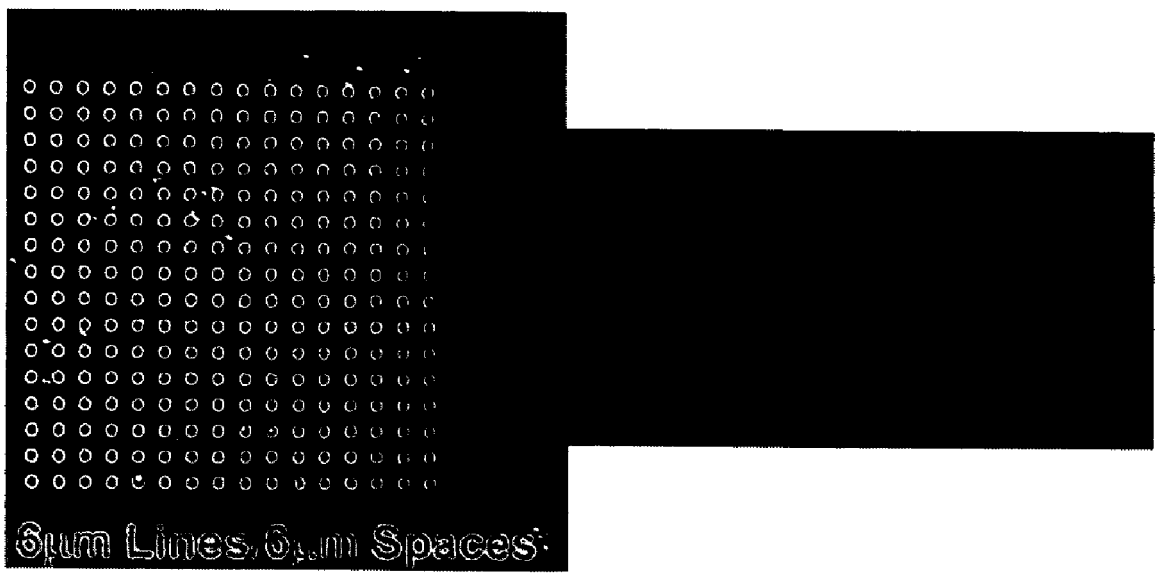
FIG. 2: Microfabricated parylene-based multi-electrode array.

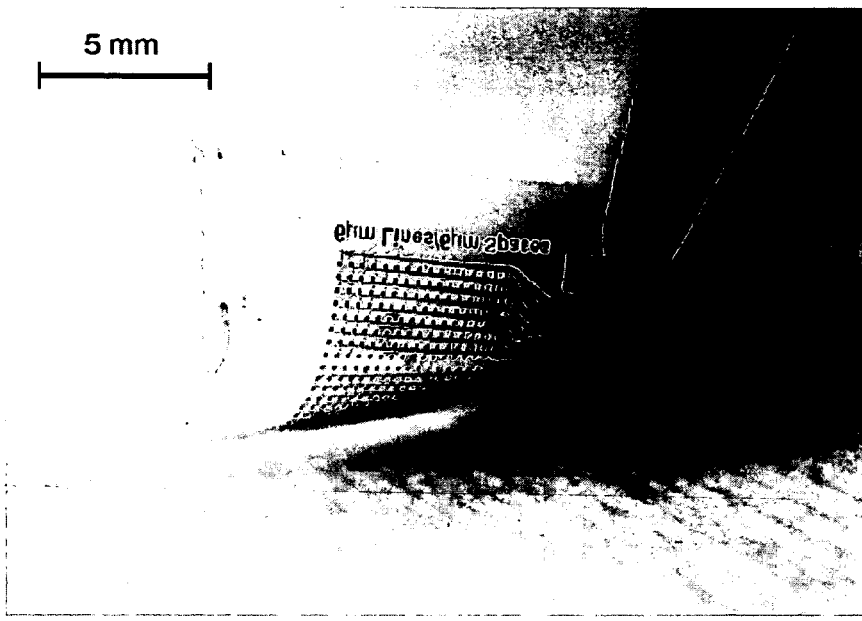
FIG. 8: Photograph of fabricated device showing device flexibility: Parylene-based multielectrode array consisting of 256 thin-film platinum electrodes. The electrodes are 125 $\mu$m in diameter, and the traces have a pitch of 12 $\mu$m.
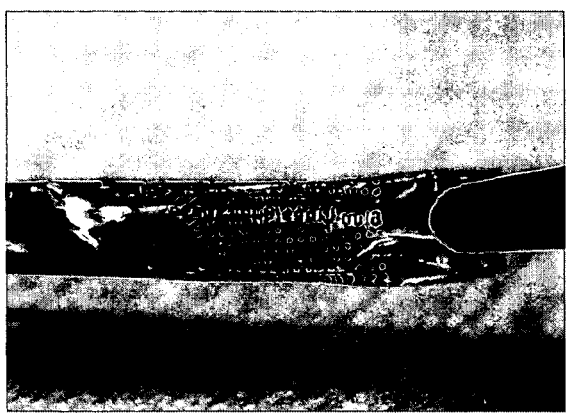
FIG. 9: Photograph of fabricated device showing device flexibility

PARYLENE-BASED FLEXIBLE MULTI-ELECTRODE ARRAYS FOR NEURONAL STIMULATION AND RECORDING AND METHODS FOR MANUFACTURING THE SAME

CROSS-REFERENCES TO RELATED APPLICATIONS

This application claims the benefit of U.S. Provisional Application 60/571,031, filed May 14, 2004, titled "PARYLENE-BASED FLEXIBLE MULTI-ELECTRODE ARRAY FOR NEURONAL STIMULATION AND RECORDING AND METHOD FOR MANUFACTURING THE SAME", which is hereby incorporated by reference in its entirety.

STATEMENT AS TO RIGHTS TO INVENTIONS MADE UNDER FEDERALLY SPONSORED RESEARCH OR DEVELOPMENT

The government may have certain rights to the invention based on National Science Foundation (NSF) Grant EEC-0310723 and EEC-9402726. NSF Grant EEC-0310723 was awarded to The California Institute of Technology ("Caltech") on Jan. 1, 2002, with Dr. Yu-Chong Tai as the Principal Investigator. NSF Grant EEC-9402726 was awarded to both Caltech and The University of Southern California ("USC") on Sep. 1, 2003, with Dr. Yu-Chong Tai as the Principal Investigator for Caltech and Dr. Mark Humayun as the Principal Investigator for USC.

BACKGROUND OF THE INVENTION

The present invention relates generally to flexible electrode arrays, and more particularly to flexible electrode arrays that are useful for neural stimulation, and methods of manufacturing the same.

Effective neural stimulation at a useful level requires microfabrication techniques to attain the necessary density of electrodes. Furthermore, materials used in the device must be biocompatible while at the same time protecting device components from the harsh environment of the body. Finally, device size and architecture are limited by the morphology of the anatomical area of interest.

Therefore, it is clear that there is a need for improved electrode arrays that are flexible in nature, formed of biocompatible material(s), and easy to manufacture and adapt.

BRIEF SUMMARY OF THE INVENTION

The present invention provides parylene-based electrode arrays, and methods for manufacturing the same, which overcome the above and other issues. Advantageously, the parylene-based electrode array devices of the present invention can be fabricated using standard integrated circuit microfabrication techniques. As such, the parylene-based devices of the present invention are capable of attaining the resolution needed in neural stimulation and recording applications and are IC compatible. Parylene is a USP Class VI biocompatible material and is approved for use in chronic implants, and has been shown to be compatible with the intraocular environment. The conformality of the parylene deposition process makes it ideal for use in hermetic sealing applications when device electronics must be shielded from the saline environment of the body. Parylene is also a very flexible, lightweight polymer and as such is optimal for matching anatomical morphology as well as for surgical implantation (e.g., the parylene array devices can be rolled up and inserted through a very small surgical incision).

According to the present invention, a parylene-based electrode array includes: 1) an underlying parylene layer, 2) one or more patterned electrode layers comprising a conductive material such as a metal, and 3) one or more overlying parylene layers. The overlying parylene is etched away or otherwise processed to expose the electrodes where stimulation or recording is to occur. All other conductive material in the device is occluded from the environment by the two layers of parylene surrounding it.

According to an aspect of the present invention, a method is provided for producing a flexible electrode array. The method typically includes providing a parylene substrate, forming a patterned conductive layer on the parylene substrate, covering the patterned conductive layer with a parylene layer, and removing a portion of the parylene layer so as to expose at least a portion of the patterned conductive layer to form an exposed electrode pattern in the parylene layer.

According to another aspect of the present invention, a flexible electrode array is provided that is typically produced by forming a patterned layer of conductive material on a parylene substrate, covering the patterned conductive layer with a parylene layer, and removing a portion of the parylene layer so as to expose at least a portion of the patterned conductive layer to form an exposed electrode pattern in the parylene layer.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1 shows the chemical structures of the three most commonly employed parylenes. Parylene C is preferred because of its mechanical strength, biocompatibility, and low moisture permeability.

FIG. 2 shows a parylene-based multi-electrode array having 256 thin-film platinum electrodes; the electrodes are 125 µm in diameter, and the traces have a pitch of 12 µm.

FIG. 8 shows a photograph of a fabricated device similar to the device of FIG. 2 showing device flexibility.

FIG. 9 is a photograph of the device of FIG. 8 (rolled up) showing its flexibility.

DETAILED DESCRIPTION OF THE INVENTION

The present invention provides parylene based electrode array devices and method of manufacturing the same. The devices according to the present invention include one or a plurality of electrodes embedded in a parylene "wrapper" comprised of a parylene substrate and one or more parylene layers covering the electrodes. Holes or apertures formed in the parylene layer(s) expose the electrodes to the external environment and allow the electrodes to stimulate or record signals depending on the application. One or several electrode layers may be formed in the parylene.

Parylene is a USP Class VI biocompatible polymer that can be deposited through a highly-conformal vapor deposition process. Types of parylene include parylene C, F, A, AM, N, and D. Of the three most common types of parylene, shown in FIG. 1, parylene C is perhaps the most widely used in industry. The advantages of the use of parylene include its proven biocompatibility, its strength and flexibility (e.g., Young's modulus ≈4 GPa), its conformal pinhole-free room-temperature deposition, its low dielectric constant (≈3) and high volume resistivity (>$10^{16}$ Ω-cm), its transparency, and its ease of manipulation using standard microfabrication techniques such as reactive ion etching (RIE). Several research groups have used parylene C deposition as a method of creating a biocompatible, water-blocking seal around electrode arrays typically fabricated using a polyimide substrate. This is necessary because most polyimides have a moisture absorption that is more than an order of magnitude higher than that of parylene C. Some specialized polyimide films have lower moisture absorption, but they require high-temperature curing steps that are generally not post-IC compatible, and their use in permanent medical implants is not permitted.

According to the present invention, parylene is used as the main substrate for fabricating an array of electrodes, minimizing the number of potential failure modes caused by the use of multiple materials, and taking full advantage of the biocompatible and mechanical properties of parylene. This innovative use of parylene as a substrate rather than as a coating material also enables simultaneous fabrication of various system components, dramatically simplifying device fabrication and ultimately the packaging of other implant devices. For example, a 16×16 multi-electrode array of parylene-embedded 125-μm-diameter planar platinum electrodes as shown in FIG. 2 has already been fabricated, and pulse testing and accelerated-lifetime saline soak testing have demonstrated its potential as a retinal stimulator. As shown in FIG. 2, multiple electrode lines are coupled with the electrode array to carry signals to and fro over an extending cable.

Figure 3:
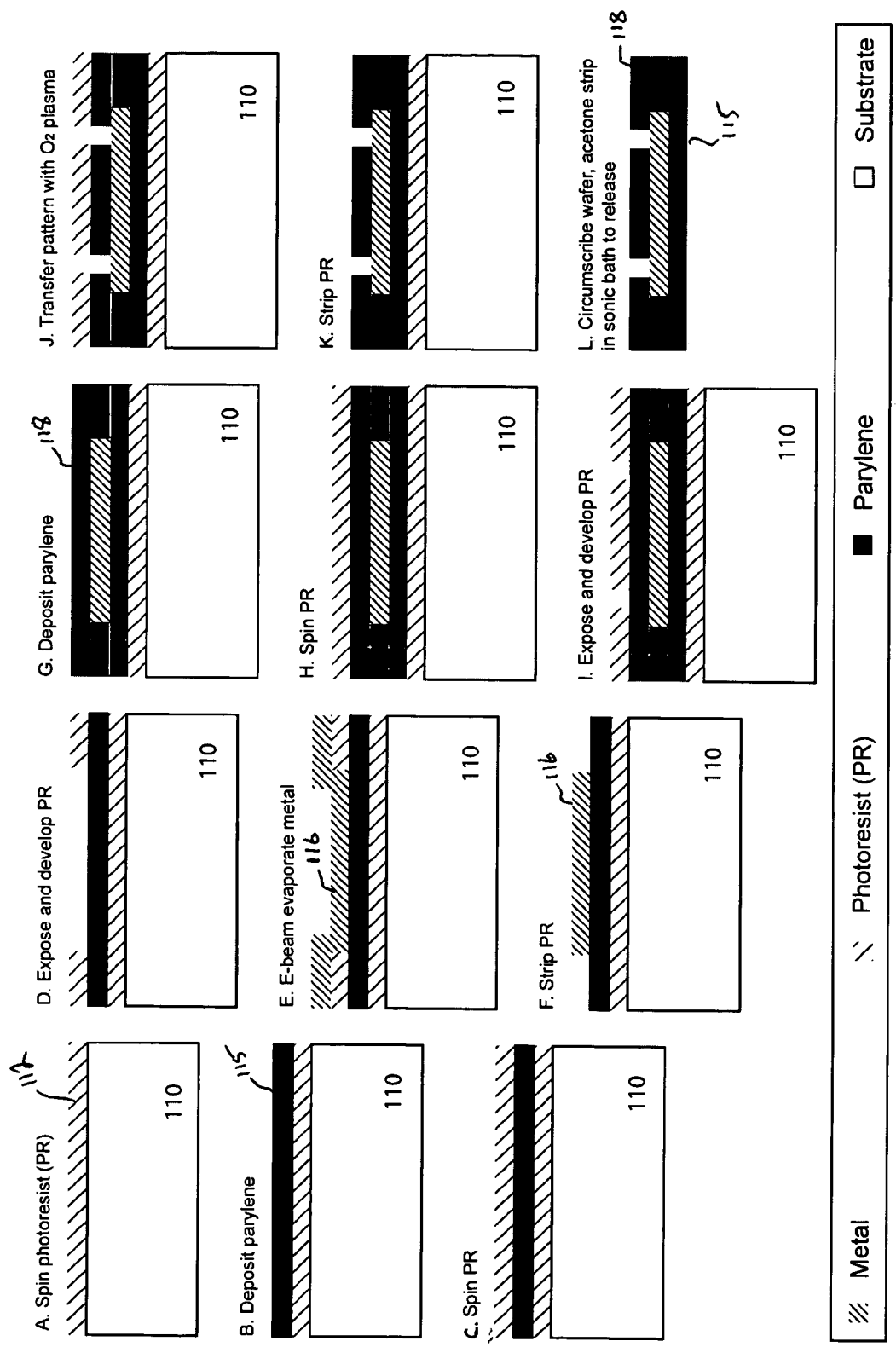
FIG. 3 illustrates an example of a process flow for fabricating a flexible electrode array device according to one embodiment.

FIG. 3 illustrates an example of a process flow for fabricating a flexible electrode array device according to one embodiment. As shown, the process begins at step 3A with the deposition of a sacrificial photoresist layer 112 on a bulk substrate material 110 such as silicon, Teflon, quartz or glass. A layer of parylene 115 is next formed on the photoresist in step 3B. The parylene layer 115 is preferably formed by deposition. Parylene layer 115 serves as the "substrate" layer for further processing. It should be appreciated that a bulk parylene block can be provided as the substrate without the use of the bulk substrate 110, however, additional steps may be required to cut or otherwise process the bulk parylene substrate to the desired thickness after the electrodes and other layers have been formed.

Steps 3C to 3F illustrate one embodiment of forming a patterned layer of conductive material on the parylene "substrate" layer 115. In step 3C, a second layer of photoresist is deposited on the parylene substrate layer 115. In step 3D, the second layer of photoresist is patterned as desired. For example using a patterned mask, the exposed photoresist is irradiated and thereafter developed as is well known to expose the underlying parylene substrate. In step 3E, conductive material 116 is deposited on the structure, and in step 3F, the photoresist is stripped or otherwise removed, leaving conductive material 116 on the parylene substrate 115 in the desired pattern. The conductive material can be deposited by evaporation, sputtering, or electroplating, for example. In preferred aspects, the conductive material includes a metal material. Useful metals include titanium, platinum, platinum grey, platinum black, chromium, gold, iridium oxide, and others. In other aspects, the conductive material includes any electrically conducting medium such as a conducting polymer, a doped semiconductor material, graphite, or a combination of these conductive materials.

Figure 6:
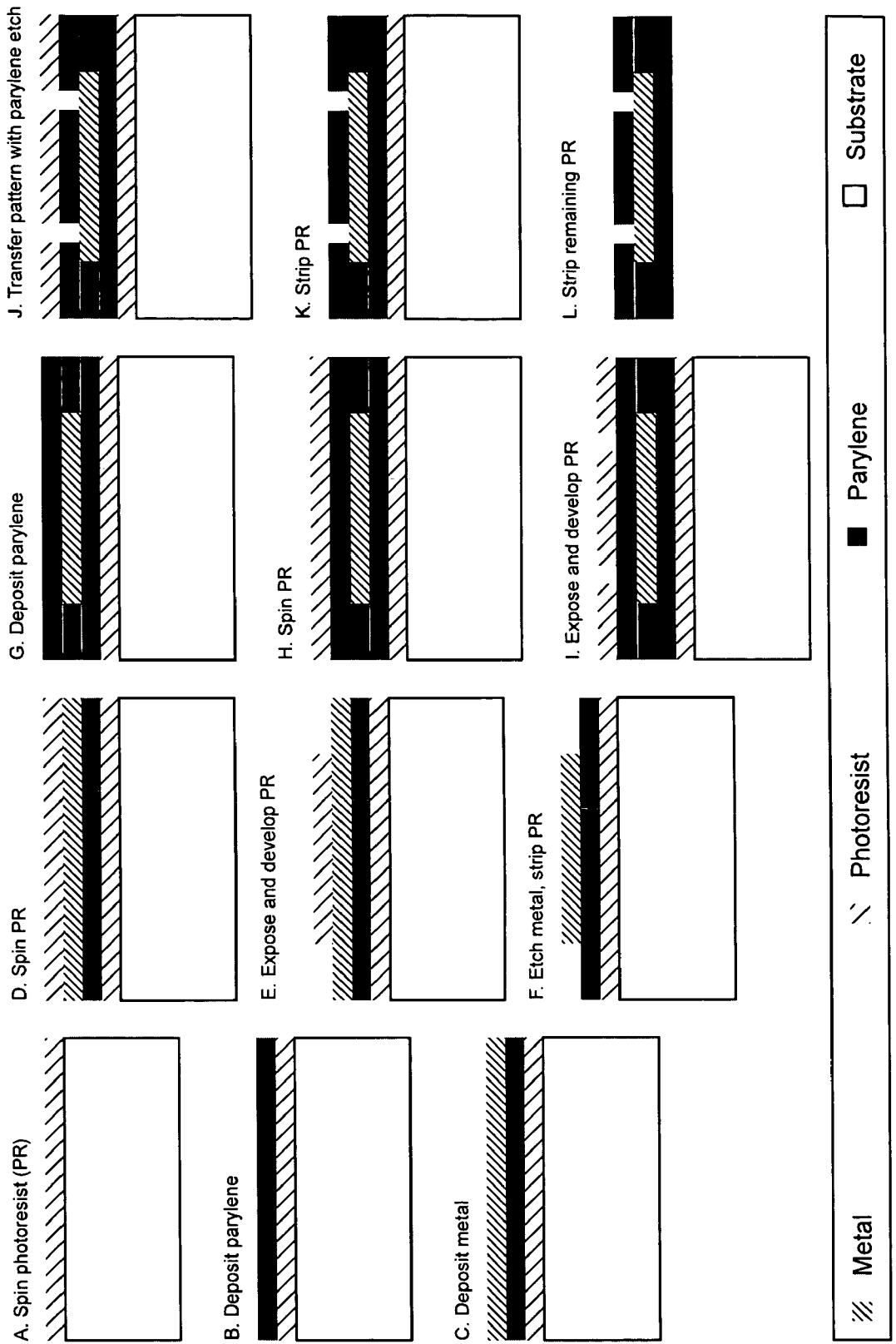
FIG. 6 illustrates another example of a process flow for fabricating a flexible electrode array device according to another embodiment.

It should be appreciated that, in an alternate embodiment to steps 3C-3F, the conductive material could be deposited first, and then a layer of photoresist deposited thereon, exposed and developed to create a desired pattern. Thereafter, the exposed conductive material could be etched or otherwise removed to create the desired pattern of conductive material on the parylene substrate. Any remaining photoresist could be removed. This alternate embodiment is shown in FIG. 6.

Returning to the embodiment shown in FIG. 3, after the conductive material 116 has been formed in the desired pattern, in step 3G, a parylene layer 118 is deposited over both the conductive material 116 and the exposed parylene substrate 115 to enclose the conductive material in parylene. In step 3H, a photoresist layer is deposited, and in step 3I, an electrode pattern is formed in the photoresist by masking, exposing and developing the photoresist as is well know. In step 3J, the electrode pattern is transferred to the parylene layer overlaying the conducting material to expose the underlying conductive material according to the desired electrode pattern. In preferred aspects, the electrode pattern is transferred by a plasma etch such as a reactive ion etch (RIE). In general useful methods for transferring the pattern to the parylene (e.g., removing parylene) include plasma etching, laser ablation, blade cutting, melting, or any combination of these processes. The preferred masking material is photoresist, however other useful materials include polymers, metals, or a shadow mask (e.g., a stencil). In step 3K, the photoresist is stripped or otherwise removed, and in step 3L, the device is removed from the bulk substrate 110 and sacrificial photoresist layer 112, e.g., using an acetone strip in a sonic bath.

It should be appreciated that devices according to the present invention are not restricted to one layer of conductive material. For example, it may be advantageous to provide a device with several alternative levels of conductors or electrodes. If, for instance, it is desirable to restrict a cable to a certain dimension but keep the lines relatively large, one line can be run out to an electrode, covered entirely, then the next line and electrode layed down, the whole structure covered in parylene, and then all the electrodes opened up. One of the electrodes would be recessed by the thickness of the parylene covering the first line and electrode. Alternately, the electrode on the first layer can be formed at the same time as the overlying line and electrode, provided the underlying trace is first opened up as by RIE or laser ablation of the parylene.

Figure 4:
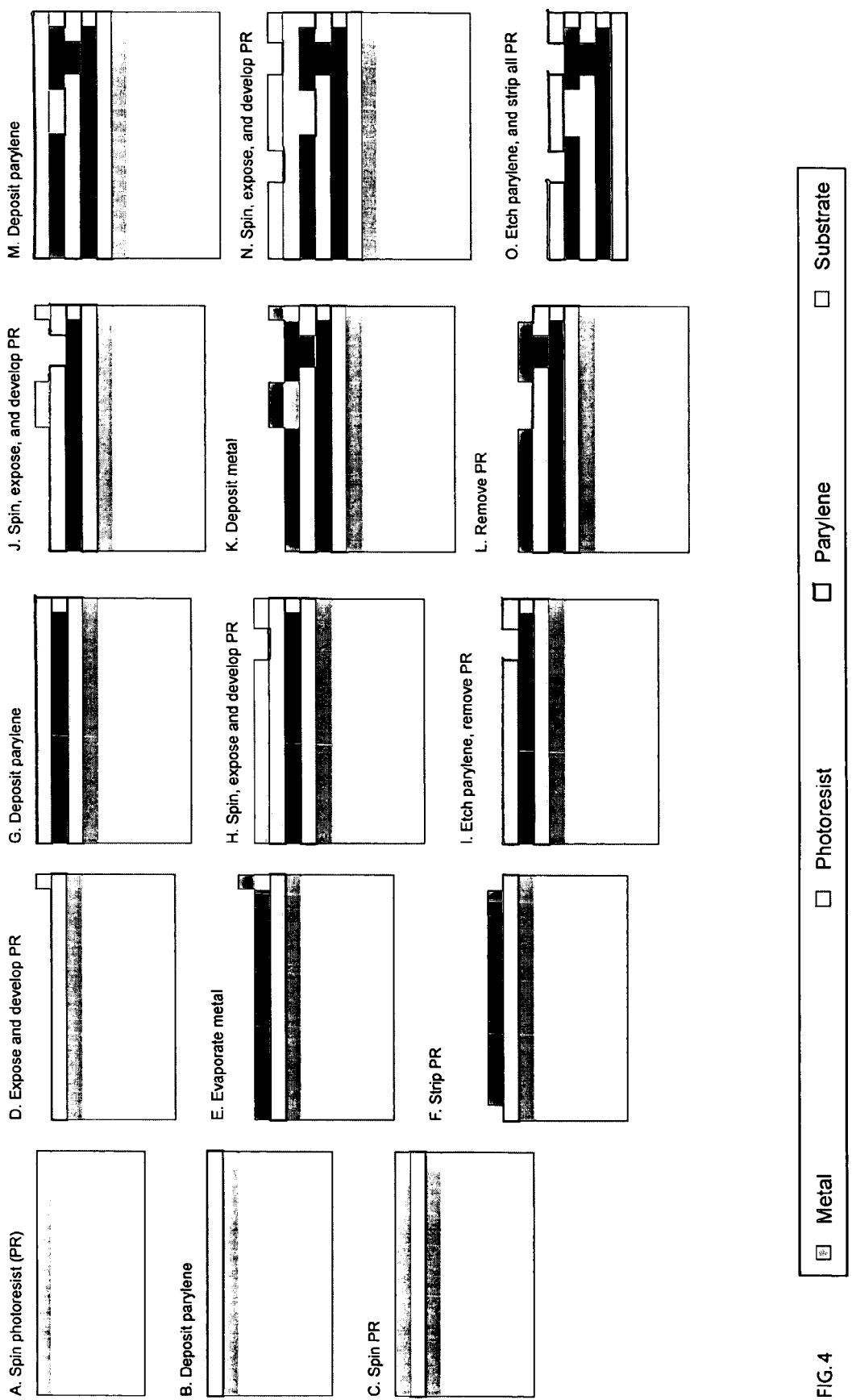
FIG. 4 illustrates an example of a process flow for fabricating a flexible electrode array device having multiple electrode layers according to one embodiment.
Figure 5:
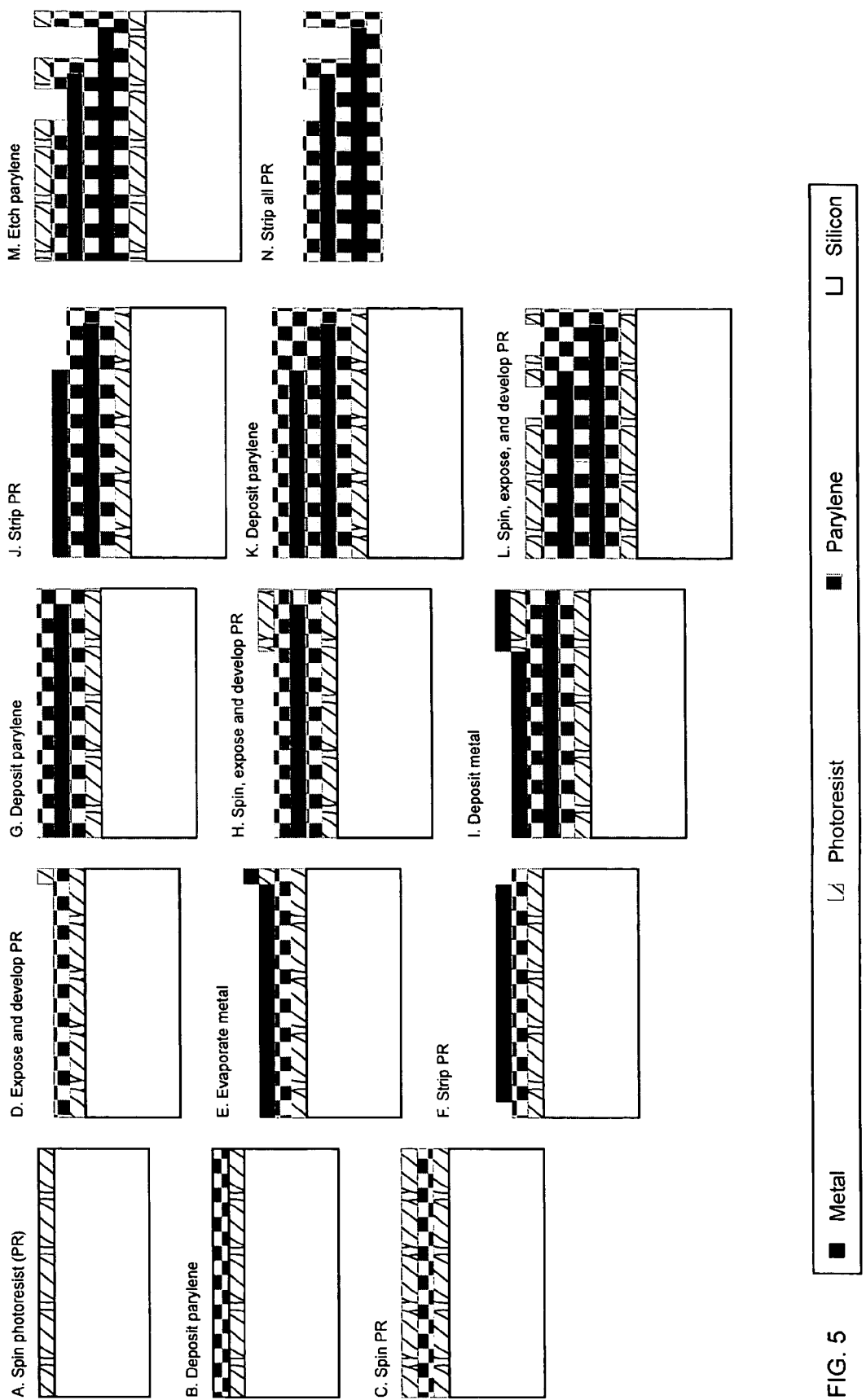
FIG. 5 illustrates an example of a process flow for fabricating a flexible electrode array device having multiple electrode layers according to another embodiment.

FIGS. 4 and 5 illustrate examples of process flows for fabricating a flexible electrode array device having multiple electrode layers according to alternate embodiments.

In FIG. 4, the steps A-I for forming the first layer of conductive material are performed in a substantially similar manner to the steps A-K of FIG. 3 and will not be discussed further. In step 4J, another layer of photoresist is deposited, and the photoresist is exposed and developed. In step 4K, a second layer of conductive material is deposited. It should be appreciated that the second layer of conductive material can be the same or different than the first layer of conductive material deposited in step 4E. In step 4L, the photoresist is stripped or otherwise removed, and in step 4M, another layer of parylene is deposited. It should be appreciated that this parylene layer can include the same or different parylene constituents as the parylene substrate layer deposited in step 4B or the parylene layer deposited in step 4G. Thereafter, in step 4N, another layer of photoresist is deposited and the photoresist is exposed and developed. In step 4Q, the pattern is transferred, for example, using a plasma etch or other parylene removal technique, and the device is removed from the bulk substrate and sacrificial photoresist layer, e.g., using an acetone strip in a sonic bath.

In FIG. 5, the steps A-G for forming the first layer of conductive material are performed in a substantially similar manner to the steps A-G of FIG. 3 and will not be discussed further. In step 5H, a layer of photoresist is deposited, exposed and developed. In step 5I, a second layer of conductive material is deposited. Again, it should be appreciated that the second layer of conductive material can be the same or different than the first layer of conductive material deposited in step 5E. In step 5J, the photoresist is removed and in step 5K another layer of parylene is deposited. Again, it should be appreciated that this parylene layer can include the same or different parylene constituents as the parylene substrate layer deposited in step 5B or the parylene layer deposited in step 5G. In step 5L, a layer of photoresist is deposited, exposed and developed, and in step 5M, the first and second parylene layers are etched or otherwise removed to expose the conductive material(s). In step 5N, the device is removed from the bulk substrate and sacrificial photoresist.

Figure 7:
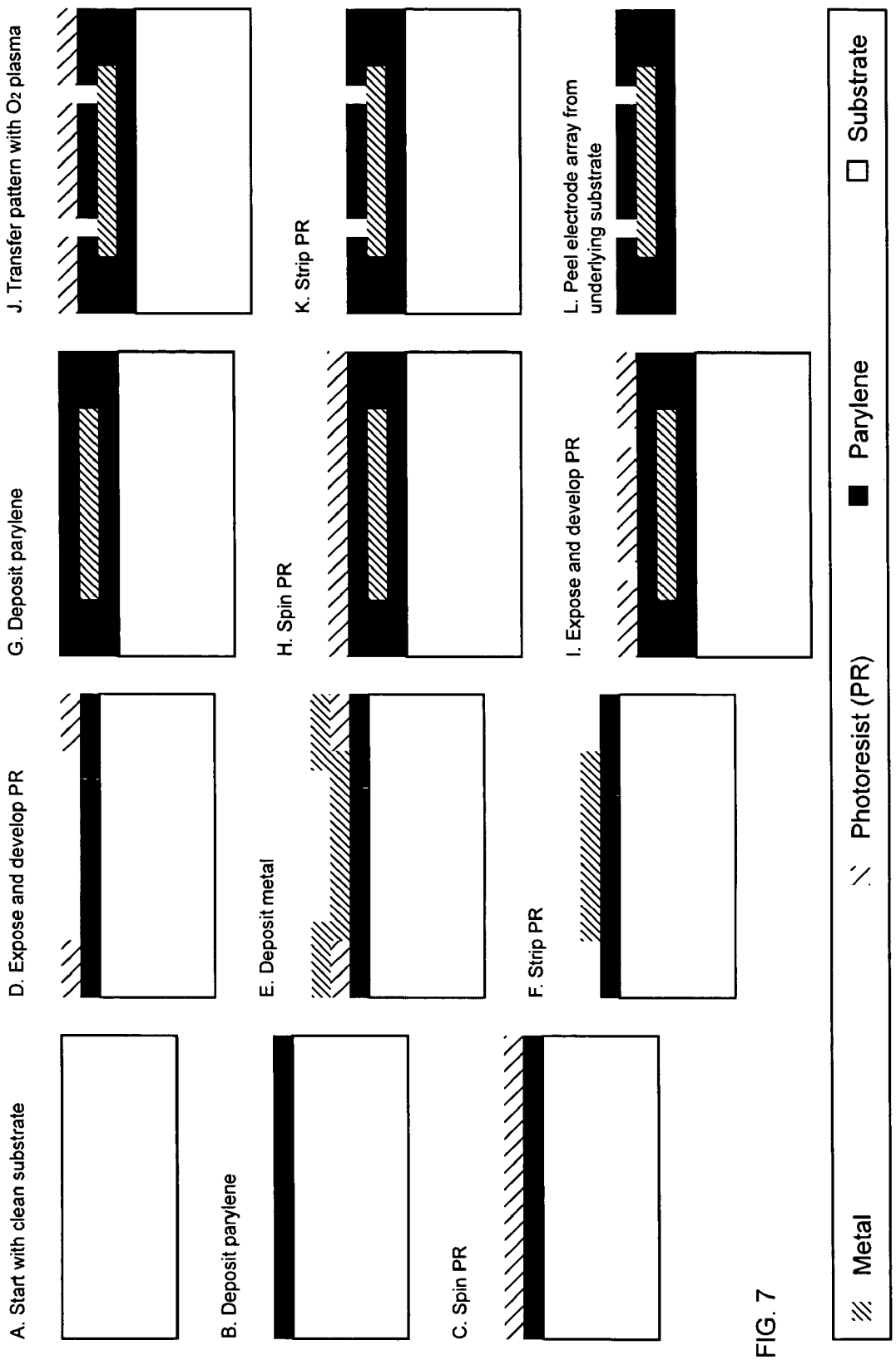
FIG. 7 illustrates another example of a process flow for fabricating a flexible electrode array device according to yet another embodiment.

FIG. 7 illustrates another example of a process flow for fabricating a flexible electrode array device according to yet another embodiment. The device produced by the process flow shown in FIG. 7 is similar to that produced as shown in FIG. 3. The process flows of FIGS. 3 and 7 are similar with the exception of steps A, B and L. In step 7A and B, the process begins with the deposition of a layer of parylene on a bulk substrate material such as silicon, Teflon, quartz or glass. No photoresist is deposited on the bulk substrate as in the FIG. 3 embodiment. The parylene layer is preferably formed by deposition. As in the FIG. 3 embodiment, the parylene layer deposited in step 7B serves as the "substrate" layer for further processing. In step 7L, the electrode array device is peeled away from the underlying bulk substrate.

In certain aspects, each "parylene" layer can be a composite layer of two or more types of parylene. For example, the parylene substrate 115 or any parylene layer such as parylene layer 118 can include parylene C with a layer of parylene F on it and another coating of parylene C, or the outer (exposed to the body) coating can be parylene A, or parylene AM for better biocompatibility. Also, a parylene layer can include a composite layer with some type of material in it to slow water permeation (for example, a metal (Ti for instance), polymer, diamond, ceramic, plastic, or (as mentioned above) parylene F).

In preferred aspects, the sizes of the holes or apertures that expose the conductive material (electrodes) are typically between about 0.005 mm to about 2 mm or larger. Thicknesses of the various layers are typically between about 1 nm to about 10,000 nm or greater. Thicknesses of individual parylene layers are preferably between about 1 μm (microns) to about 100 microns or more. Also, the number of electrodes formed on an electrode array can vary from 1 electrode to about 100,000 electrodes or more. An electrode array can be formed in any geometric shape such as a square or circular shape; typically the size of the array will be on the order of about 0.1 mm to about 2 cm, square or in diameter, depending in part on the number of electrodes in the array. Overall, the length of an electrode cable can be on the order of about 0.1 mm to about 10 cm or greater.

According to one embodiment, the conductive electrodes are formed of carbonized parylene. This obviates the need for having any metal exposed to the environment. Parylene can be carbonized either by exposing it in a hot furnace (preferably unoxygenated gas like nitrogenous gas) or by ion bombardment/implantation of parylene with carbon atoms. In the latter case, a mask can be used to mask off those areas that should not be carbonized (e.g., using a stencil, photoresist, metal, or other masking means). Other conductive materials or polymers could also be used. For example, to form carbonized parylene electrodes, in FIG. 3, steps 3C through 3F could be replaced with the steps of depositing a second parylene layer, masking the layer, carbonizing the unmasked parylene and removing excess, un-carbonized parylene (e.g., using plasma etch or other method of removal) from the second parylene layer.

FIGS. 8 and 9 are photographs of a fabricated device similar to the device of FIG. 2 showing device flexibility. FIG. 9 shows the device rolled up, ready for surgical insertion.

According to additional aspects of the present invention, the top and bottom layers of the parylene can be treated, for example, with an oxygen plasma, to increase hydrophilicity. Parylene when deposited is quite hydrophobic, but if placed in oxygen plasma for a brief amount of time, the surface can be made more hydrophilic so that implantation and wetting of the device can be made easier. Additionally, the parylene surfaces can be otherwise chemically modified so as to enable better attachment or biological activity in the region of interest. Preferably such treatments are performed after a device has been fabricated. Also, the device can be heat-formed (e.g., around a mold) so as to give it curvature or other morphology to conform better to a desired structure. For example, in retinal prosthesis applications, a device can be adapted to conform to the retina.

While the invention has been described by way of example and in terms of the specific embodiments, it is to be understood that the invention is not limited to the disclosed embodiments. To the contrary, it is intended to cover various modifications and similar arrangements, in addition to those discussed above, as would be apparent to those skilled in the art. For example, a metal layer (e.g. titanium) can also be added to the outside of the parylene "skin" to further hermetically seal the device. Therefore, the scope of the appended claims should be accorded the broadest interpretation so as to encompass all such modifications and similar arrangements.

What is claimed is:

1. A method of producing a flexible electrode array, the method comprising:
   providing a parylene substrate wherein said substrate is formed by directly depositing a parylene layer onto a bulk substrate block;
   forming a patterned conductive layer on the parylene substrate;
   covering the patterned conductive layer with a parylene layer; and
   removing a portion of the parylene layer so as to expose at least a portion of the patterned conductive layer to form an exposed electrode pattern in the parylene layer, wherein the patterned conductive layer comprises carbonized parylene.

2. A method of producing a flexible electrode array, the method comprising:
   providing a parylene substrate;
   forming a patterned conductive layer on the parylene substrate wherein the patterned conductive layer comprises carbonized parylene;
   covering the patterned conductive layer with a parylene layer; and
   removing a portion of the parylene layer so as to expose at least a portion of the patterned conductive layer to form an exposed electrode pattern in the parylene layer.

3. The method of claim 2, wherein the patterned conductive layer comprises a conductive metal selected from the group consisting of gold, platinum, chromium, titanium, platinum and iridium oxide.

4. The method of claim 2, wherein the parlyene substrate and the parylene layer each comprise one or more of parylene A, parylene C, parylene AM, parylene F, parylene N or parylene D.

5. The method of claim 2, wherein providing a parylene substrate includes depositing parylene on a layer of photoresist overlaying a bulk substrate.

6. The method of claim 5, further comprising separating the parylene substrate from the photoresist layer.

7. The method of claim 2, wherein forming the patterned conductive layer comprises:
   depositing a layer of photoresist on the parylene substrate;
   patterning the photoresist with a mask;
   removing the patterned photoresist to expose the parylene substrate;
   depositing a conductive material on the exposed parylene substrate; and
   removing the photoresist.

8. The method of claim 7, wherein depositing a conductive material includes one of an e-beam evaporation process, a sputtering process or an electroplating process.

9. The method of claim 2, wherein forming the patterned conductive layer comprises:
   depositing a layer of conductive material on the parylene substrate;
   patterning the conductive material with a mask;
   removing exposed conductive material to expose the parylene substrate; and
   removing the mask.

10. The method of claim 2, wherein removing a portion of the parylene layer comprises:
    depositing a layer of photoresist on the parylene layer;
    patterning the photoresist with a mask;
    removing the patterned photoresist to expose portions of the parylene layer; and
    etching the exposed portions of the parylene layer.

11. The method of claim 2, wherein the patterned conductive layer includes a conductive material selected from the group consisting of a conducting polymer, a doped semiconductor, and graphite.

12. The method of claim 2, wherein removing a portion of the parylene layer comprises one of a plasma etch process, a laser ablation process, a blade cutting process or a melting process.

13. The method of claim 2, further comprising:
    forming a second patterned conductive layer on the parylene layer; and
    covering the second patterned conductive layer with a second parylene layer.

14. The method of claim 13, wherein removing a portion of the parylene layer occurs before the step of covering the second patterned conductive layer with a second parylene layer.

15. The method of claim 13, wherein removing a portion of the parylene layer occurs after the step of covering the second patterned conductive layer with a second parylene layer.

16. The method of claim 2, further comprising the following steps in order: treating a device comprising the parylene substrate and the parylene layer with an oxygen plasma, and exposing said substrate and layer to said oxygen plasma for a sufficient amount of time to increase the hydrophilicity of said parylene, said exposure easing implantation and wetting of said device.

* * * * *